United States Patent
Cers

(10) Patent No.: US 11,523,926 B2
(45) Date of Patent: Dec. 13, 2022

(54) DYNAMIC LUMBAR REALIGNMENT SYSTEM

(71) Applicant: Peteris Alberts Cers, Minneapolis, MN (US)

(72) Inventor: Peteris Alberts Cers, Minneapolis, MN (US)

(73) Assignee: Peteris Alberts Cers, Minneapolis, MN (US)

( * ) Notice: Subject to any disclaimer, the term of this patent is extended or adjusted under 35 U.S.C. 154(b) by 1235 days.

(21) Appl. No.: 14/814,885

(22) Filed: Jul. 31, 2015

(65) Prior Publication Data

US 2016/0030224 A1 Feb. 4, 2016

Related U.S. Application Data

(63) Continuation of application No. PCT/US2015/043074, filed on Jul. 31, 2015.
(Continued)

(51) Int. Cl.
*A61F 5/02* (2006.01)

(52) U.S. Cl.
CPC .................... *A61F 5/028* (2013.01)

(58) Field of Classification Search
CPC ...... A61F 5/0104; A61F 5/028; A61F 5/0193; A61F 5/01; A61F 5/24–28;
(Continued)

(56) References Cited

U.S. PATENT DOCUMENTS 2,775,767 A * 1/1957 Gould .................... A41C 1/003
  450/106
3,524,449 A * 8/1970 Peters ...................... A41C 1/00
  450/100

(Continued)

FOREIGN PATENT DOCUMENTS

CN 102470040 A 5/2012
CN 102470240 A 5/2012
(Continued)

OTHER PUBLICATIONS

International Patent Application No. PCT/US2015/043074, International Search Report and Written Opinion dated Dec. 3, 2015, 6 pages.
(Continued)

*Primary Examiner* — Michelle J Lee
(74) *Attorney, Agent, or Firm* — Fredrikson & Byron, P.A.

(57) ABSTRACT

A dynamic lumbar realignment system is provided. A stabilizing and compressive strap is configured to be positioned onto a body garment with a pelvic cover, a waistband, a left thigh short sleeve and a right thigh short sleeve or is configured to be positioned onto a user with a pelvis, a waist, a left thigh and a right thigh along a therapeutic orientation path. The stabilizing and compressive strap comprises a first strap end and a second strap end. The therapeutic orientation path comprises a beginning and an end. The first strap end is fixed at the beginning while the second strap end is fixed at the end. The stabilizing and compressive strap is arranged along the therapeutic orientation path in such a way that abdominal compression, pelvic tilt and thigh rotation are dynamically integrated so as to provide and generate a therapeutic effect.

7 Claims, 20 Drawing Sheets

Related U.S. Application Data

(60) Provisional application No. 62/031,242, filed on Jul. 31, 2014.

(58) Field of Classification Search
CPC ......... A61F 5/00–0104; A61F 5/02–03; A41C 1/003; A41C 1/006; A41C 1/00–04; A41C 1/08; A41C 1/10; A41D 13/0015; A41D 13/0017; A41D 13/00–0007
See application file for complete search history.

(56) References Cited

U.S. PATENT DOCUMENTS

| | | | | |
|---|---|---|---|---|
| 5,486,194 | A * | 1/1996 | Kawasaki | A61B 17/1325 602/53 |
| 5,928,175 | A * | 7/1999 | Tanaka | A61F 5/028 602/75 |
| 6,105,169 | A * | 8/2000 | Colorado | A62B 35/0025 2/81 |
| 7,074,204 | B2 * | 7/2006 | Fujii | A41C 1/003 602/75 |
| 7,559,093 | B2 * | 7/2009 | Sudo | A63B 21/4001 2/69 |
| 7,631,366 | B2 * | 12/2009 | Oyama | A41C 1/003 2/69 |
| 8,235,173 | B2 * | 8/2012 | Kopp | A62B 35/0012 182/7 |
| 2004/0116260 | A1 * | 6/2004 | Drennan | A63B 21/0004 482/124 |
| 2006/0074365 | A1 * | 4/2006 | Brown | A61F 13/143 602/62 |
| 2011/0000005 | A1 * | 1/2011 | Brown | A61F 5/0111 2/227 |
| 2014/0207040 | A1 | 7/2014 | Ingimundarson et al. | |

FOREIGN PATENT DOCUMENTS

| | | |
|---|---|---|
| CN | 103190971 A | 7/2013 |
| CN | 203029434 U | 7/2013 |
| RU | 2165752 C1 | 4/2001 |
| WO | 2011010257 A1 | 1/2011 |
| WO | 2014108132 A1 | 7/2014 |

OTHER PUBLICATIONS

European Patent Application No. 15826727.8, Extended European Search Report dated Dec. 11, 2017, 7 pages.

* cited by examiner

DYNAMIC LUMBAR REALIGNMENT SYSTEM

The current application claims benefit of U.S. Provisional Patent application Ser. No. 62/031,242 filed on Jul. 31, 2014, and is a continuation of PCT Patent Application PCT/US15/43074 filed Jul. 31, 2015 which claims benefit of U.S. Provisional Patent application Ser. No. 62/031,242 filed on Jul. 31, 2014.

FIELD OF THE INVENTION

The present invention relates generally to a lumbar realignment system for back support and posture improvement as well as variants thereof. More specifically, the present invention is a dynamic lumbar realignment system for providing abdominal compression as well as providing pelvic tilt with thigh rotation that automatically adjusts based on the user's movement.

BACKGROUND OF THE INVENTION

Back pain and injuries cause significant difficulties in everyday life due to the inconveniences of limited mobility preventing or hindering normal activity. The lower back (lumbar region) in particular is susceptible to pain and injuries due to the large amount of body weight that is supported by the region. Back pain and injuries can be caused and exacerbated by a number of factors. Sports injuries, poor form when lifting heavy objects, poor posture, excessive strain, and sudden force exerted on the bones, muscles, and other tissues of the back can result in chronic or acute back pain. Another factor potentially causing chronic back pain is deviations of the spine from its natural curve. Conditions such as lumbar hyperlordosis are caused by tight and/or weak muscles around the hip and spine that cause an imbalance and result in excessive curvature of the spine. Lumbar hyperlordosis is not a permanent condition and as such, may be reversed and corrected. The condition may be corrected by performing a variety of lower back, hip-flexor and hamstring muscle stretches as well as exercises aimed at strengthening the abdominal muscles. There are various types of corrective garments available as well, such as braces. However, conventional braces and similar garments serve only to immobilize the problematic lumbar region of the spine. Immobilization not only fails to address the issue of excessive spine curvature, but causes additional complications such as limiting the user's freedom of movement due to the constriction of the immobilizing garment. This constriction can also cause gas flow inhibition and result in discomfort and pain.

The present invention is a dynamic lumbar realignment system having the features of claim 1. Further embodiments are subject-matter of the dependent claims. The dynamic lumbar realignment system according to the invention serves to provide moderate abdominal compression while simultaneously moving the lumbar region of the spine back into normal alignment. This is accomplished by free-floating dynamic strap moving the lumbar region back into proper alignment while the user's thighs are simultaneously rotated. The excessive spine curvature that is characteristic of lumbar hyperlordosis is thus corrected and the user is stimulated to better overall posture. The compression provided by the present invention does not inhibit the user's gas flow, resulting in no discomfort or pain. The present invention is designed to aid in the user's ability to regain optimal posture such that the user's muscles are able to retrain to fire in proper alignment to regain proper muscle memory. Excessive weight and injuries can create difficulties in maintaining proper posture and correct form during dynamic activities. As such, the present invention is able to assist these types of users in optimal recovery and subsequently pain-free lives.

DETAIL DESCRIPTIONS OF THE INVENTION

All illustrations of the drawings are for the purpose of describing selected versions of the present invention and are not intended to limit the scope of the present invention.

The present invention is a dynamic lumbar realignment system for back support and overall posture improvement. The present invention functions by providing a level of abdominal compression while simultaneously tilting the pelvis back and rotating the thighs inward to reduce or prevent back pain due to lumbar hyperlordosis. The present invention does not inhibit natural movement and is capable of dynamically responding to the user's body movement when worn while providing a corrective effect via elastic resistance. The present invention is available in additional variants to address related issues as well.

Figure 1:
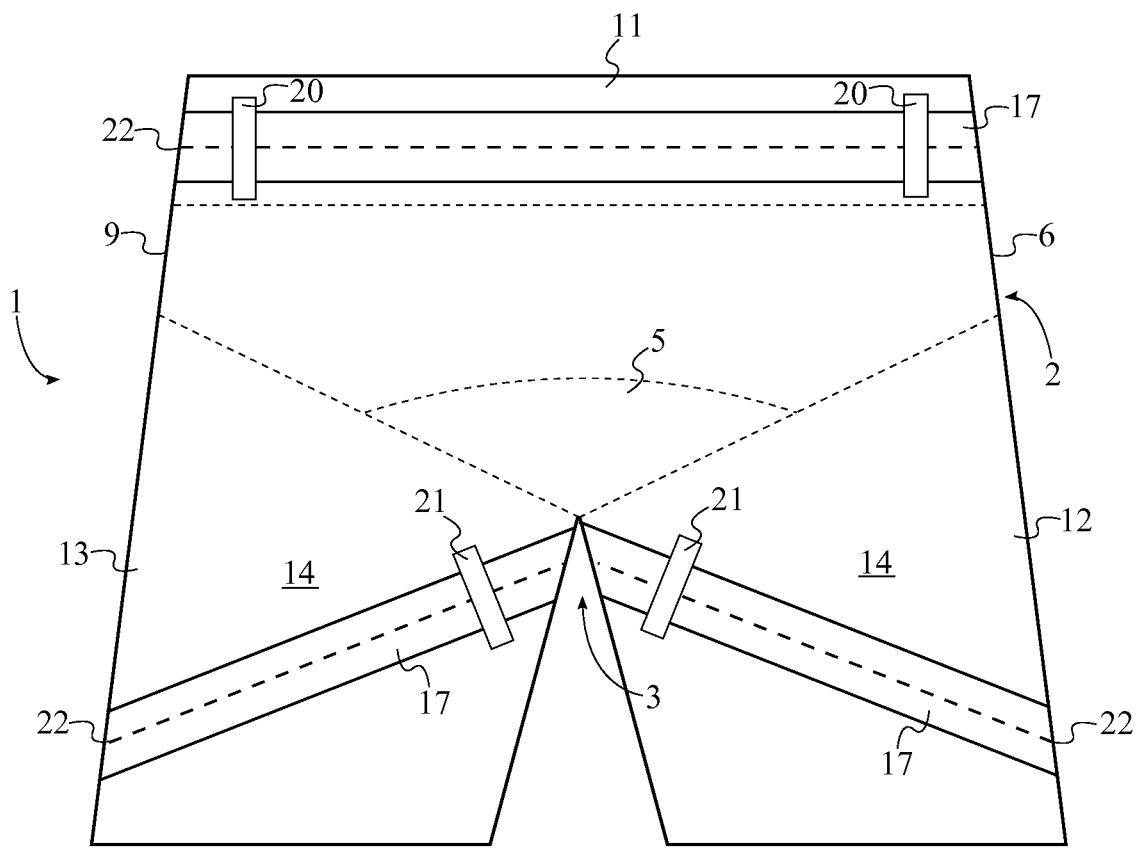
FIG. 1 is a front diagrammatic view depicting the therapeutic orientation path.
Figure 2:
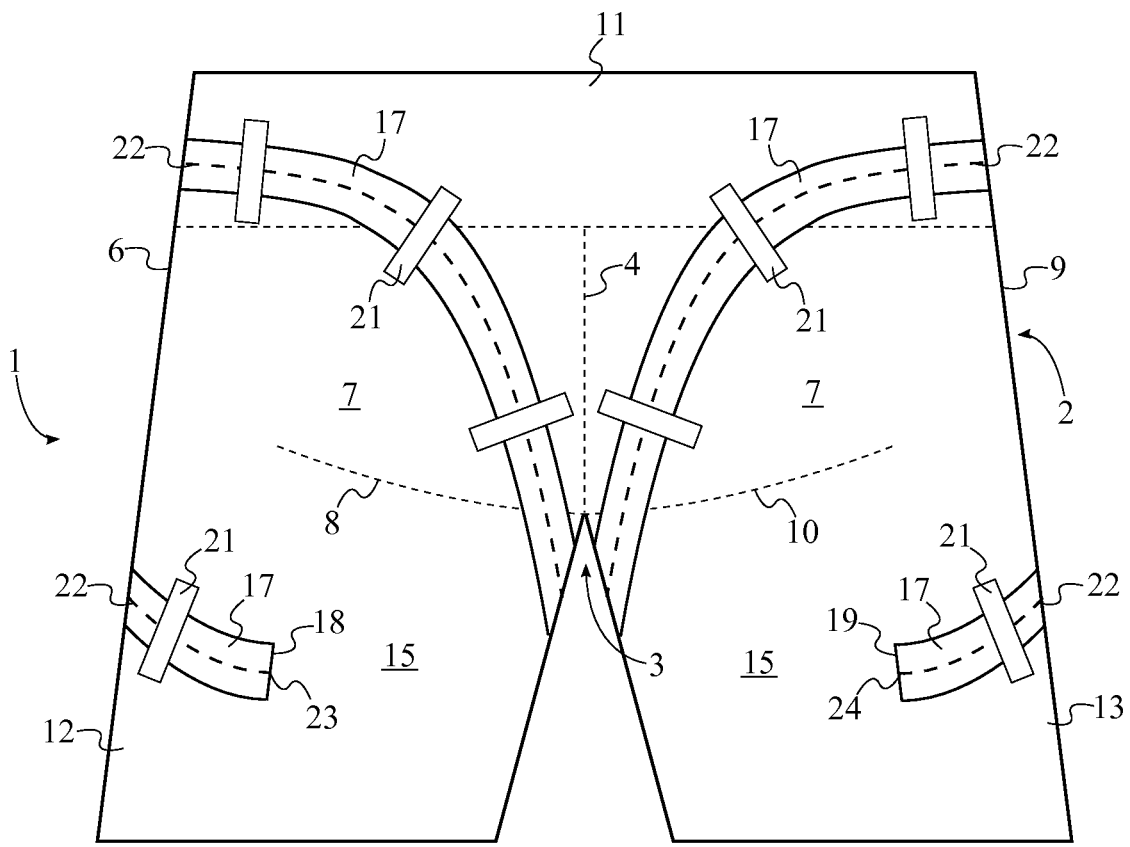
FIG. 2 is a rear diagrammatic view depicting the therapeutic orientation path.

The present invention is shown in FIG. 1 and FIG. 2 and comprises a compressive lower body garment 1, a stabilizing strap 17, a plurality of strap-supporting attachment points 20, and a plurality of strap-guiding attachment points 21. The compressive lower body garment 1 is preferably composed of an elastic material and provides a moderate or tolerable degree of abdominal compression. The abdominal compression exerted by the compressive lower body garment 1 does not inhibit the user's natural gas flow. Additionally, the abdominal compression exerted by the compressive lower body garment 1 may be even milder in order to accommodate certain users (e.g. pregnant users). The compressive lower body garment 1 comprises a pelvic cover 2, a waistband 11, a left leg short sleeve 12, and a right leg short sleeve 13. The pelvic cover 2 is the portion of the compressive lower body garment 1 that encompasses the user's groin, buttock, and crotch regions. The waistband 11 is the portion of the compressive lower body garment 1 that encircles the user's waist and lower abdomen when the compressive lower body garment 1 is worn. The waistband 11 may vary in size to accommodate all users (e.g. pregnant users who may require a larger waistband 11). The left leg short sleeve 12 and the right leg short sleeve 13 are able to accommodate the user's left leg and the user's right leg, respectively. The left leg short sleeve 12 and the right leg short sleeve 13 each comprise an anterior region 14 and a posterior region 15 that are oppositely positioned towards the respectively front and back portions of the left leg short sleeve 12 and the right leg short sleeve 13. The compressive lower garment additionally serves as a surface onto which the stabilizing strap 17 may be fastened.

The plurality of strap-supporting attachment points 20 is designed to hold the stabilizing strap 17 securely in place about the waistband 11 and as such, the plurality of strap-supporting attachment points 20 is externally positioned about the waistband 11. The plurality of strap-guiding attachment points 21 is designed to guide the stabilizing strap 17 along the pelvic cover 2, the left leg short sleeve 12, and the right leg short sleeve 13. Additionally, the plurality of strap-guiding attachment points 21 is able to hold the stabilizing strap 17 securely in place on the pelvic cover 2, the left leg short sleeve 12, and the right leg short sleeve 13. As such, the plurality of strap-guiding attachment points 21 is externally positioned onto the pelvic cover 2, the left leg short sleeve 12, and the right leg short sleeve 13.

Figure 18:
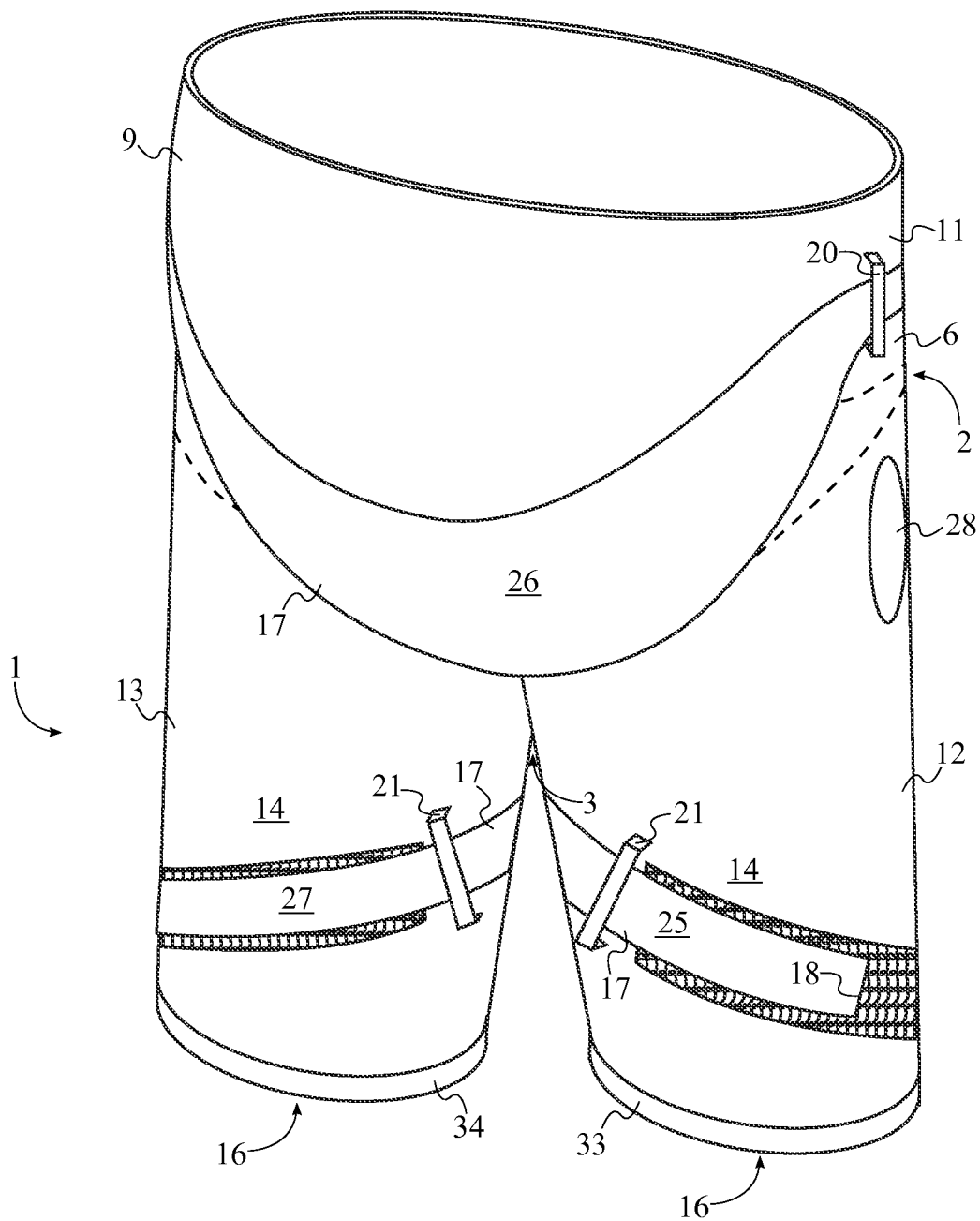
FIG. 18 is a front perspective view of the pregnancy variant of the present invention.

The stabilizing strap 17 is utilized to tilt the user's pelvis back and additionally rotates the user's thighs inward, exerting a corrective effect via elastic resistance. The stabilizing strap 17 comprises a first strap end 18 and a second strap end 19 that serve as opposite ends of the stabilizing strap 17. The stabilizing strap 17 is positioned through a combination of selected loops from the plurality of strap-guiding attachment points 21 and the plurality of strap-supporting attachment points 20. This prevents the stabilizing strap 17 from shifting due to the user's natural movement when worn along with the compressive lower body garment 1. As shown in FIG. 1 and FIG. 2, the combination of selected loops is defined by a therapeutic orientation path 22 for the stabilizing strap 17. The therapeutic orientation path 22 positions the stabilizing strap 17 onto the compressive lower body garment 1 in order to alter the user's posture. The first strap end 18 is fixed at a beginning 23 of the therapeutic orientation path 22 while the second strap end 19 is fixed at an end 24 of the therapeutic orientation path 22. This ensures that the stabilizing strap 17 does not separate from the compressive lower body garment 1 when the present invention is in use. The stabilizing strap 17 is preferably secured to the compressive lower body garment 1 using hook and loop fasteners or a similar mechanism. The stabilizing strap 17 is composed of an elastic material in order to allow the user to adjust the pressure exerted on the compressive lower body garment 1 when the stabilizing strap 17 is attached to the compressive lower body garment 1. The stabilizing strap 17 may vary in terms of size as well to accommodate all users (e.g. pregnant users). A pregnancy variant of the present invention is shown in FIG. 18.

The stabilizing strap 17 may be sewn or otherwise integrated into the compressive lower body garment 1. In this case, the plurality of strap-supporting attachment points 20 and the plurality of strap-guiding attachment points 21 are stitching integrating the stabilizing strap 17 into the compressive lower body garment 1. If the stabilizing strap 17 is stitched or otherwise integrated into the compressive lower body garment 1, the stabilizing strap 17 is positioned in a manner that reflects the therapeutic orientation path 22. Alternatively, the stabilizing strap 17 may be free-floating and entirely separable from the compressive lower body garment 1. In this case, each of the plurality of strap-supporting attachment points 20 and each of the plurality of strap-guiding attachment points 21 is a loop externally mounted to the compressive lower body garment 1. The loops are positioned in a manner that reflects the therapeutic orientation path 22. As such, the stabilizing strap 17 may be routed through any of the loops in order to achieve the desired therapeutic effect.

Figure 20:
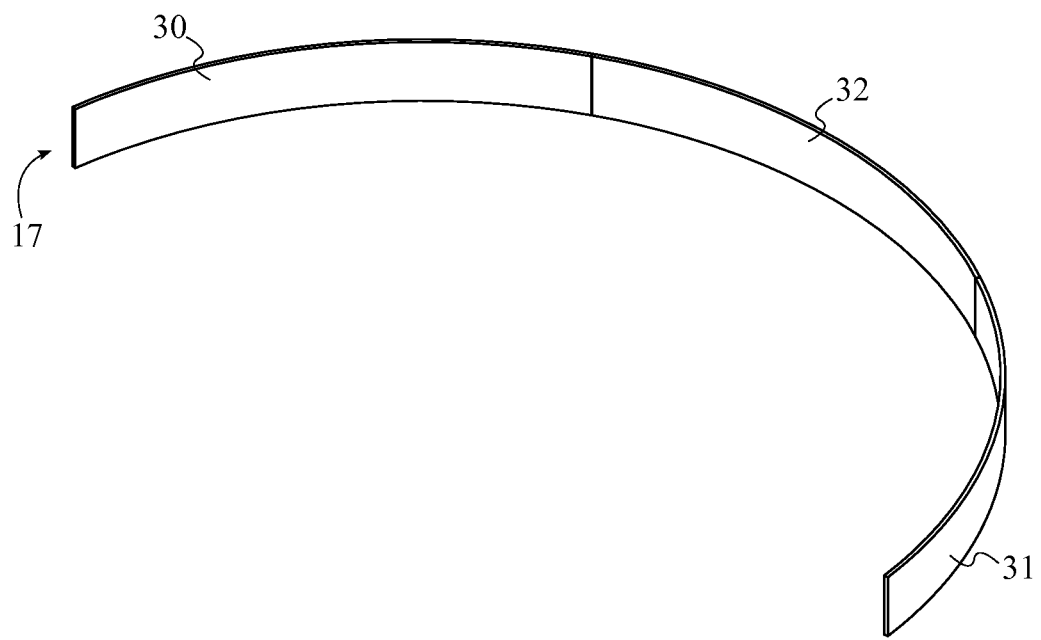
FIG. 20 is a front perspective view of a stabilizing strap with elastic and non-elastic section.

The stabilizing strap 17 may be partially elastic or fully elastic. In a partially elastic embodiment of the present invention shown in FIG. 20, the present invention further comprises a first elastic section 30, a second elastic section 31, and a non-elastic section 32. The first elastic section 30 and the second elastic section 31 are adjustable in length and exert pressure on the user's body when the present invention is in use. Conversely, the non-elastic section 32 is not adjustable in length and does not exert pressure on the user's body. In this embodiment of the present invention, the first elastic section 30 is connected adjacent to the non-elastic section 32 while the second elastic section 31 is connected adjacent to the non-elastic section 32, opposite to the first elastic section 30. This positions the non-elastic section 32 in between the first elastic section 30 and the second elastic section 31. The positioning of the non-elastic section 32 ensures that no elasticity or pressure is present on the iliac crest, eliminating any potential discomfort.

The compressive lower body garment 1 and the stabilizing strap 17 may include a means for assigning the amount of force that is applied to the user's pelvis and how much force is applied to the user's thighs. For example, the compressive lower body garment 1 and the stabilizing strap 17 may each include one or more sections of higher surface tension that allow the user to assign the desired amount of force on his or her pelvis and thighs. This is particularly suitable for users who are experiencing varying degrees of pain throughout their bodies.

Figure 3:
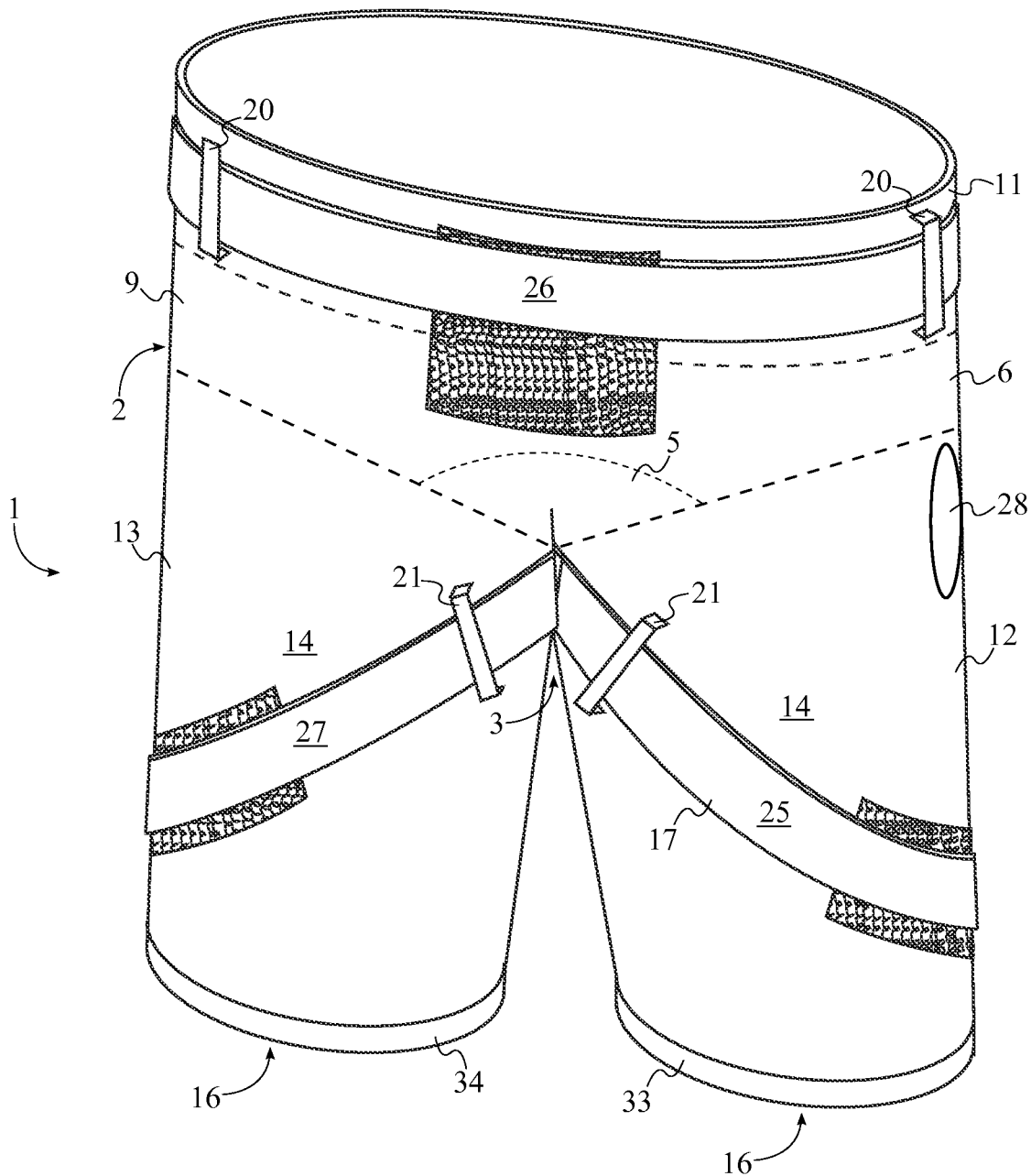
FIG. 3 is a front perspective view of the lumbar hyperlordosis variant of the present invention.
Figure 4:
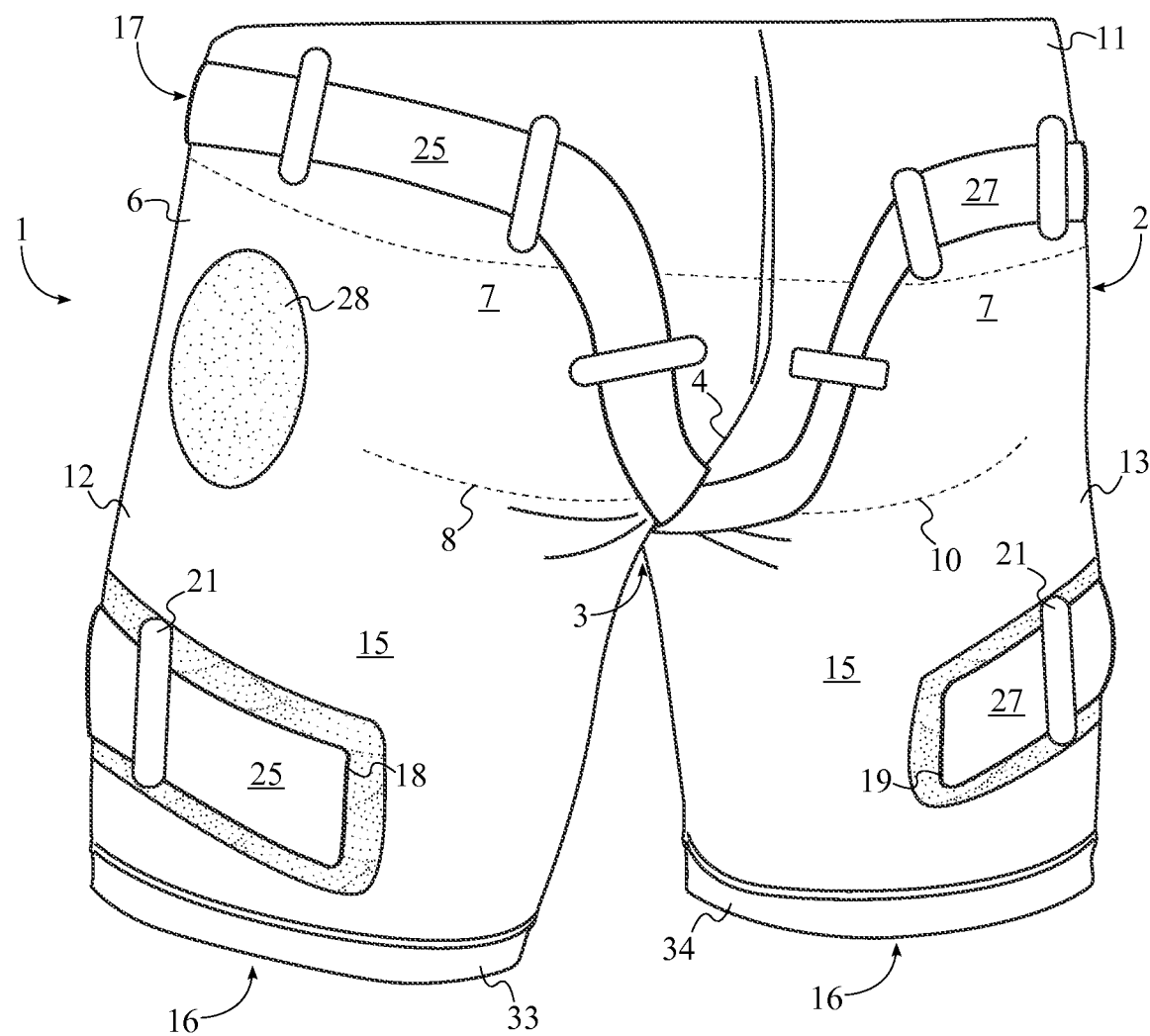
FIG. 4 is a rear perspective view of the lumbar hyperlordosis variant of the present invention.

The lumbar hyperlordosis variant of the present invention shown in FIG. 3 and FIG. 4 is designed to address abnormal or excessive curvature of the back. In the lumbar hyperlordosis variant of the present invention, the therapeutic orientation path 22 positions the stabilizing strap 17 onto the compressive lower body garment 1 in a manner such that the user's pelvis is tilted back and the thighs are rotated inward. The beginning 23 of the therapeutic orientation path 22 is located at the posterior region 15 of the left leg short sleeve 12, opposite to the pelvic cover 2. This positions the first strap end 18 away from the pelvic cover 2 and allows the stabilizing strap 17 to wrap around the left leg short sleeve 12. A first portion 25 of the therapeutic orientation path 22 traverses from the beginning 23 of the therapeutic orientation path 22, about the left leg short sleeve 12 from the posterior region 15 to the anterior region 14, adjacent to a crotch region 3 of the pelvic cover 2, adjacent to a buttock crevice region 4 of the pelvic cover 2, and to a second portion 26 of the therapeutic orientation path 22. When the stabilizing strap 17 traverses about the left leg short sleeve 12 from the posterior region 15 to the anterior region 14, the user's left thigh is rotated inward. The stabilizing strap 17 then traverses through the crotch region 3 and toward the buttock crevice region 4, positioning the stabilizing strap 17 in a manner such that the user's left thigh is rotated inward. The second portion 26 of the therapeutic orientation path 22 traverses from the first portion 25 of the therapeutic orientation path 22, about the waistband 11, and to a third portion 27 of the therapeutic orientation path 22. In this embodiment of the present invention, the stabilizing strap 17 traverses about the waistband 11 in a manner such that the user's pelvis is tilted back. The third portion 27 of the therapeutic orientation path 22 traverses from the second portion 26 of the therapeutic orientation path 22, adjacent to the buttock crevice region 4, adjacent to the crotch region 3, about the right leg short sleeve 13 from the anterior region 14 to the posterior region 15, and to the end 24 of the therapeutic orientation path 22. The stabilizing strap 17 traverses adjacent to the buttock crevice region 4 and the crotch region 3 in order to begin rotating the user's right thigh inward. The stabilizing strap 17 then traverses about the right leg short sleeve 13 from the anterior region 14 to the posterior region 15 in order to further rotate the user's right thigh inward. The end 24 of the therapeutic orientation path 22 is located at the posterior region 15 of the right leg short sleeve 13, opposite to the pelvic cover 2, positioning the second strap end 19 away from the pelvic cover 2 and allowing the stabilizing strap 17 to wrap around the right leg short sleeve 13.

Figure 5:
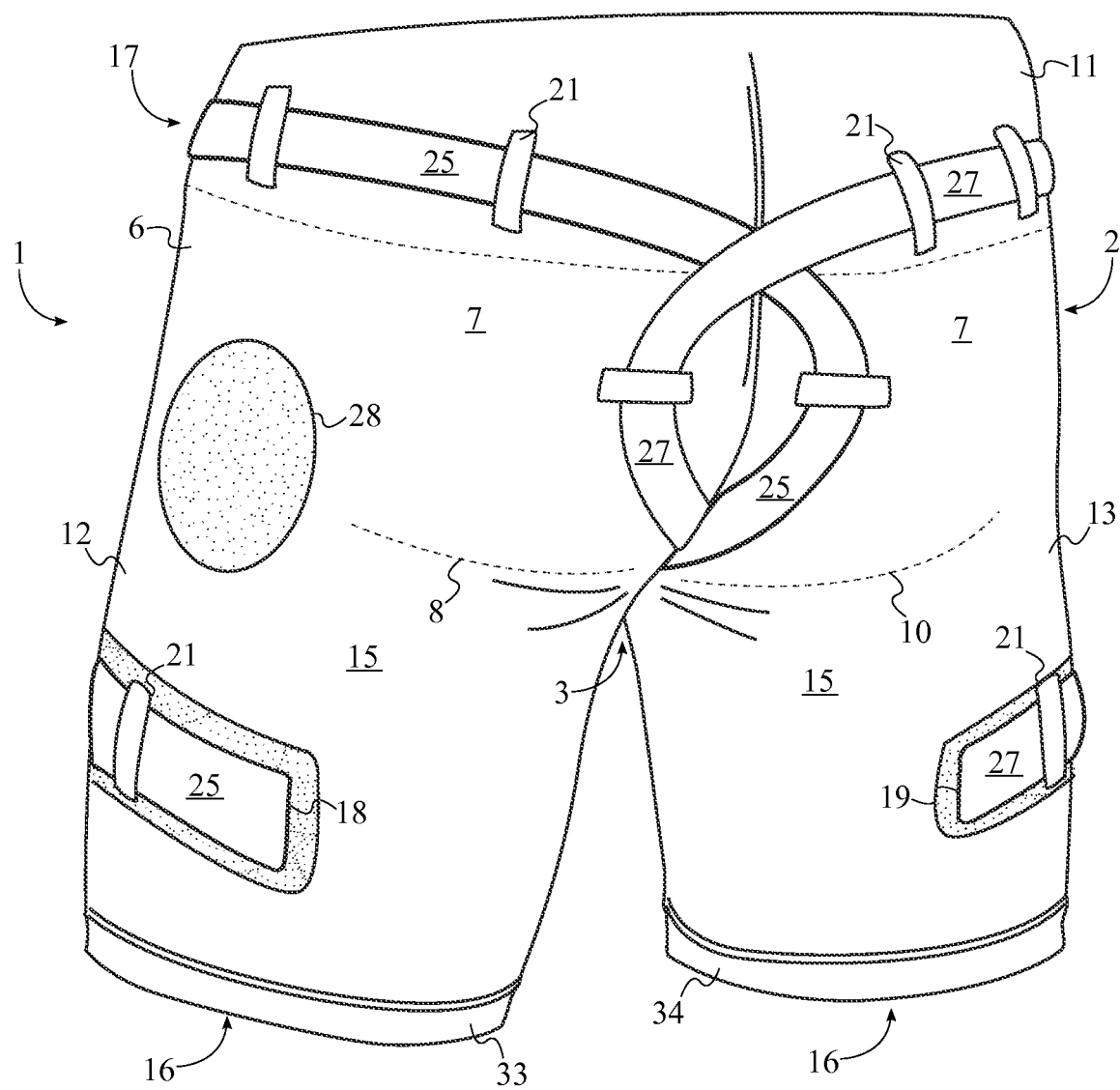
FIG. 5 is a rear perspective view of the lumbar hyperlordosis variant of the present invention with intersecting stabilizing strap.

In the embodiment of the present invention shown in FIG. 3 and FIG. 4, the first portion 25 of the therapeutic orientation path 22 and the third portion 27 of the therapeutic orientation path 22 traverse adjacent to each other on the buttock crevice region 4. This allows the stabilizing strap 17 to tilt the user's pelvis back while simultaneously rotating the user's thighs inward. However, the embodiment of the present invention shown in FIG. 5 displays an alternate arrangement for the first portion 25 of the therapeutic orientation path 22 and the third portion 27 of the therapeutic orientation path 22. The first portion 25 of the therapeutic orientation path 22 and the third portion 27 of the therapeutic orientation path 22 intersect each other on the buttock crevice region 4. This exerts the same effect of tilting the user's pelvis back while rotating the user's thighs inward.

Figure 6:
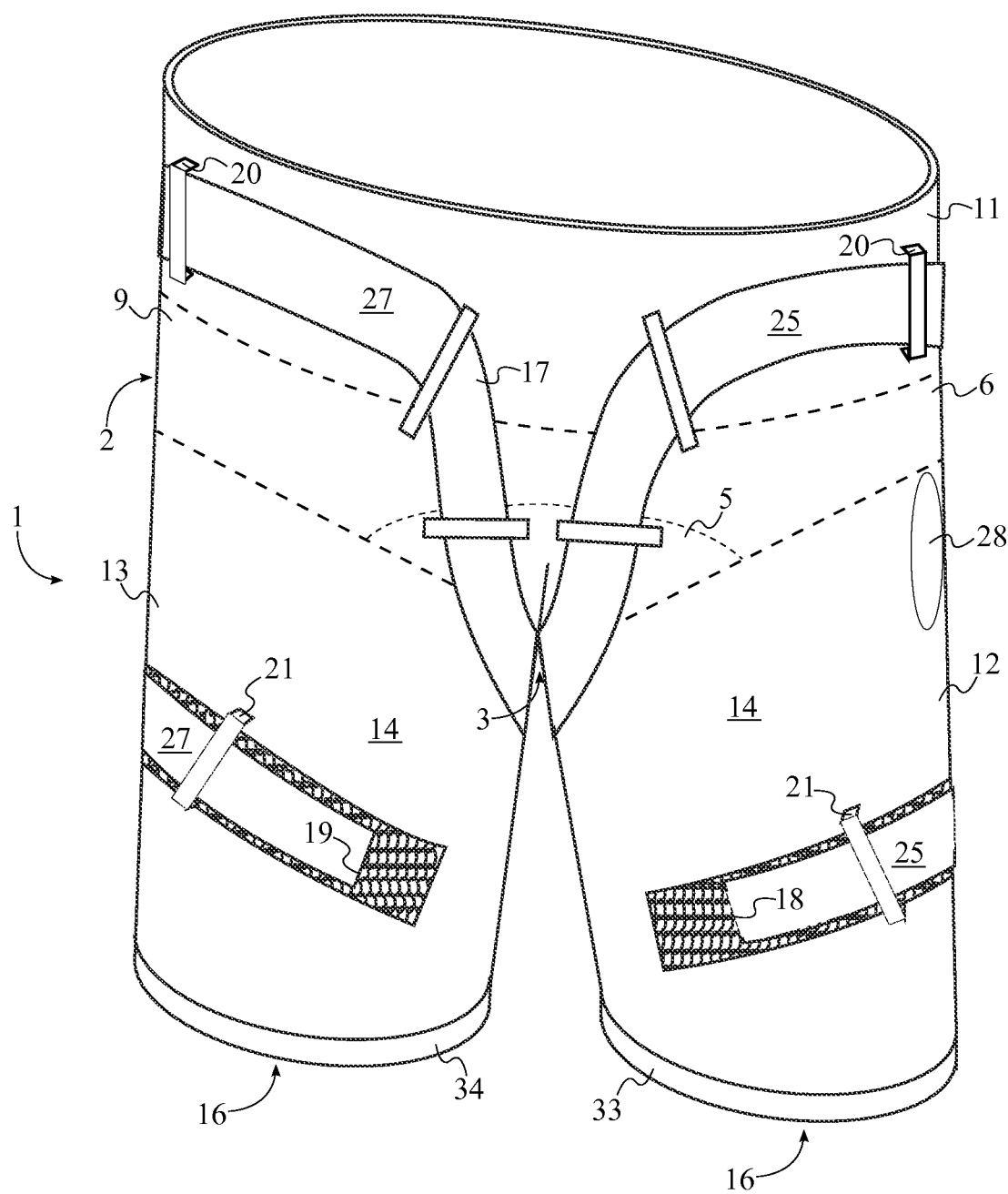
FIG. 6 is a front perspective view of the lumbar hypolordosis variant of the present invention.
Figure 7:
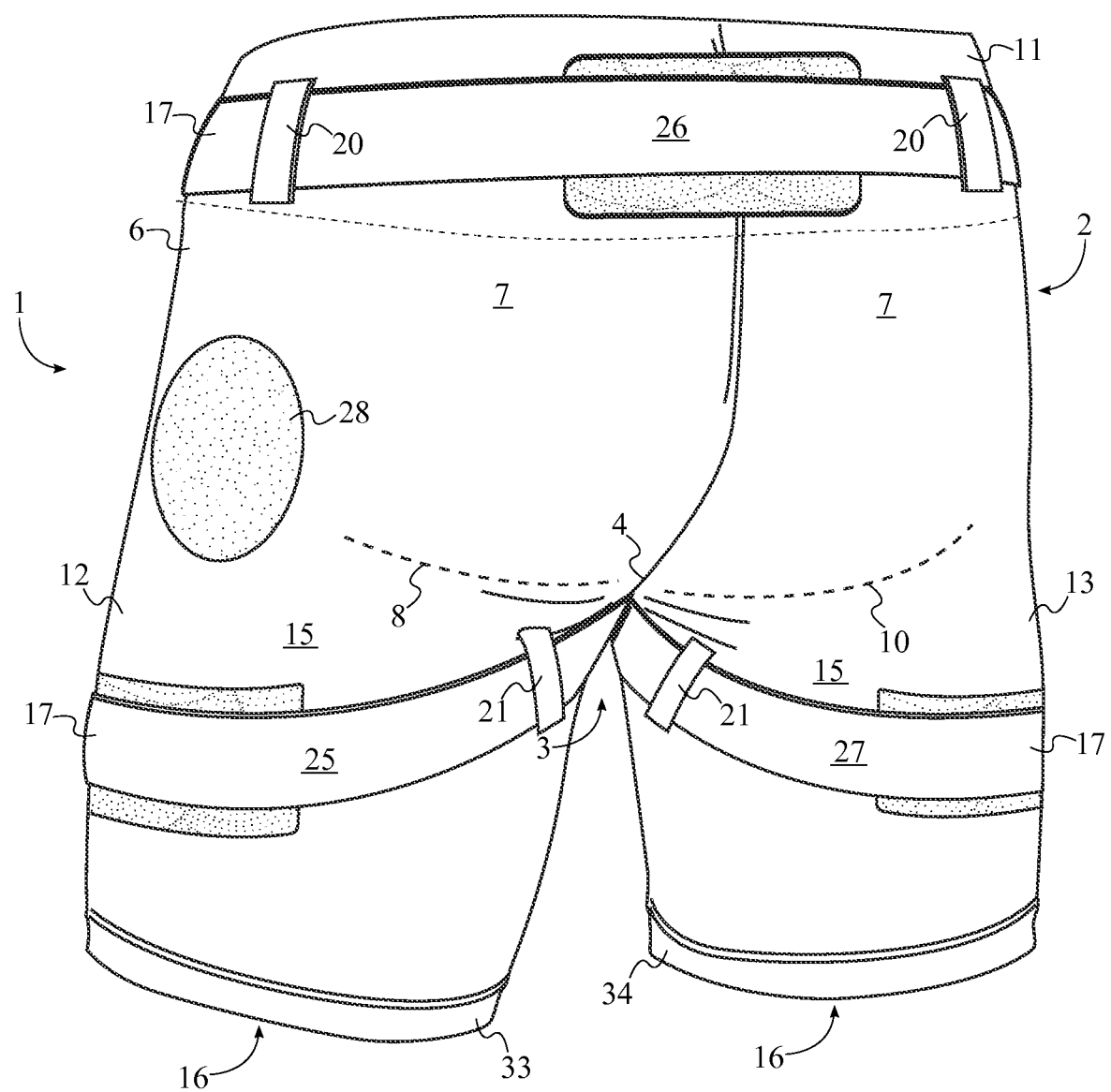
FIG. 7 is a rear perspective view of the lumbar hypolordosis variant of the present invention.

The lumbar hypolordosis variant of the present invention shown in FIG. 6 and FIG. 7 is primarily intended to address an abnormal lack of lumbar curvature and as such, is designed to exert the opposite effect on the user's body as the lumbar hyperlordosis variant. In the lumbar hypolordosis variant of the present invention, the therapeutic orientation path 22 positions the stabilizing strap 17 onto the compressive lower body garment 1 in a manner such that the user's pelvis is tilted forward and the thighs are rotated outward. The beginning 23 of the therapeutic orientation path 22 is located at the anterior region 14 of the left leg short sleeve 12, opposite to the pelvic cover 2. The first strap end 18 is thus positioned away from the pelvic cover 2 and the stabilizing strap 17 is allowed to wrap around the left leg short sleeve 12. A first portion 25 of the therapeutic orientation path 22 traverses from the beginning 23 of the therapeutic orientation path 22, about the left leg short sleeve 12 from the anterior region 14 to the posterior region 15, adjacent to the crotch region 3, adjacent to the groin region 5, and to a second portion 26 of the therapeutic orientation path 22. The stabilizing strap 17 is able to rotate the user's left thigh outward when traversing about the left leg short sleeve 12 from the anterior region 14 to the posterior region 15. The stabilizing strap 17 then traverses through the crotch region 3 toward the groin region 5, further positioning the stabilizing strap 17 to rotate the user's left thigh outward. The second portion 26 of the therapeutic orientation path 22 traverses from the first portion 25 of the therapeutic orientation path 22, about the waistband 11, and to a third portion 27 of the therapeutic orientation path 22. In this embodiment of the present invention, the stabilizing strap 17 traverses about the waistband 11 in a manner such that the user's pelvis is tilted forward. The third portion 27 of the therapeutic orientation path 22 traverses from the second portion 26 of the therapeutic orientation path 22, adjacent to the groin region 5, adjacent to the crotch region 3, about the right leg short sleeve 13 from the posterior region 15 to the anterior region 14, and to the end 24 of the therapeutic orientation path 22. The stabilizing strap 17 traverses adjacent to the groin region 5 and the crotch region 3 in order to begin rotating the user's right thigh outward. The stabilizing strap 17 then traverses about the right leg short sleeve 13 from the posterior region 15 to the anterior region 14 in order to further rotate the user's right thigh outward. The end 24 of the therapeutic orientation path 22 is located at the anterior region 14 of the right leg short sleeve 13, opposite to the pelvic cover 2. The second strap end 19 is thus positioned away from the pelvic cover 2 and the stabilizing strap 17 is able to wrap around the right leg short sleeve 13.

Figure 8:
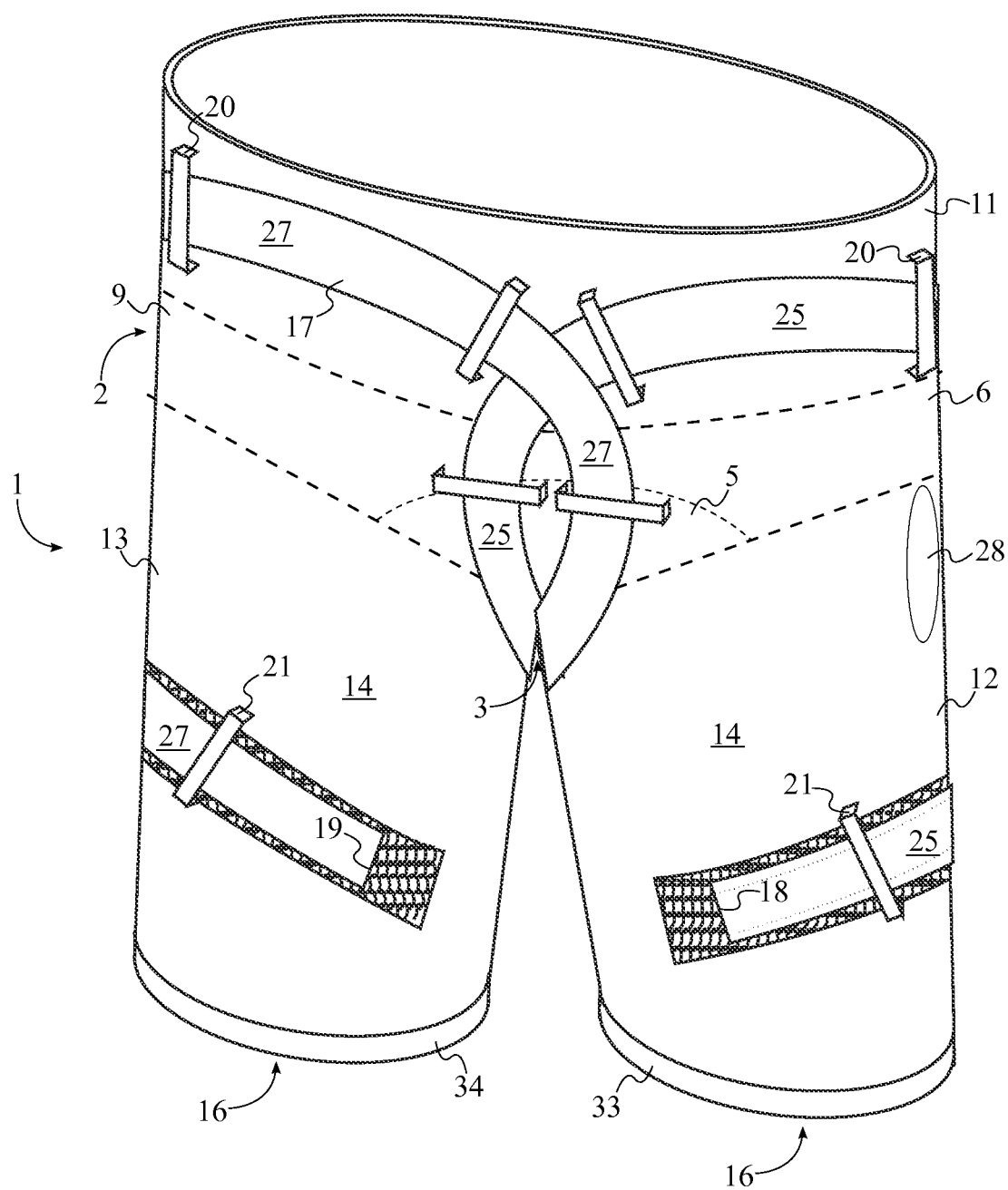
FIG. 8 is a front perspective view of the lumbar hypolordosis variant of the present invention with intersecting stabilizing strap.

In the embodiment of the present invention shown in FIG. 6 and FIG. 7, the first portion 25 of the therapeutic orientation path 22 and the third portion 27 of the therapeutic orientation path 22 traverse adjacent to each other on the groin region 5. The stabilizing strap 17 is thus able to tilt the user's pelvis forward while simultaneously rotating the user's thighs outward. The embodiment of the present invention shown in FIG. 8 displays an alternate arrangement for the first portion 25 of the therapeutic orientation path 22 and the third portion 27 of the therapeutic orientation path 22. The first portion 25 of the therapeutic orientation path 22 and the third portion 27 of the therapeutic orientation path 22 intersect each other on the groin region 5. However, this exerts the same effect of tilting the user's pelvis forward while rotating the user's thighs outward.

Figure 9:
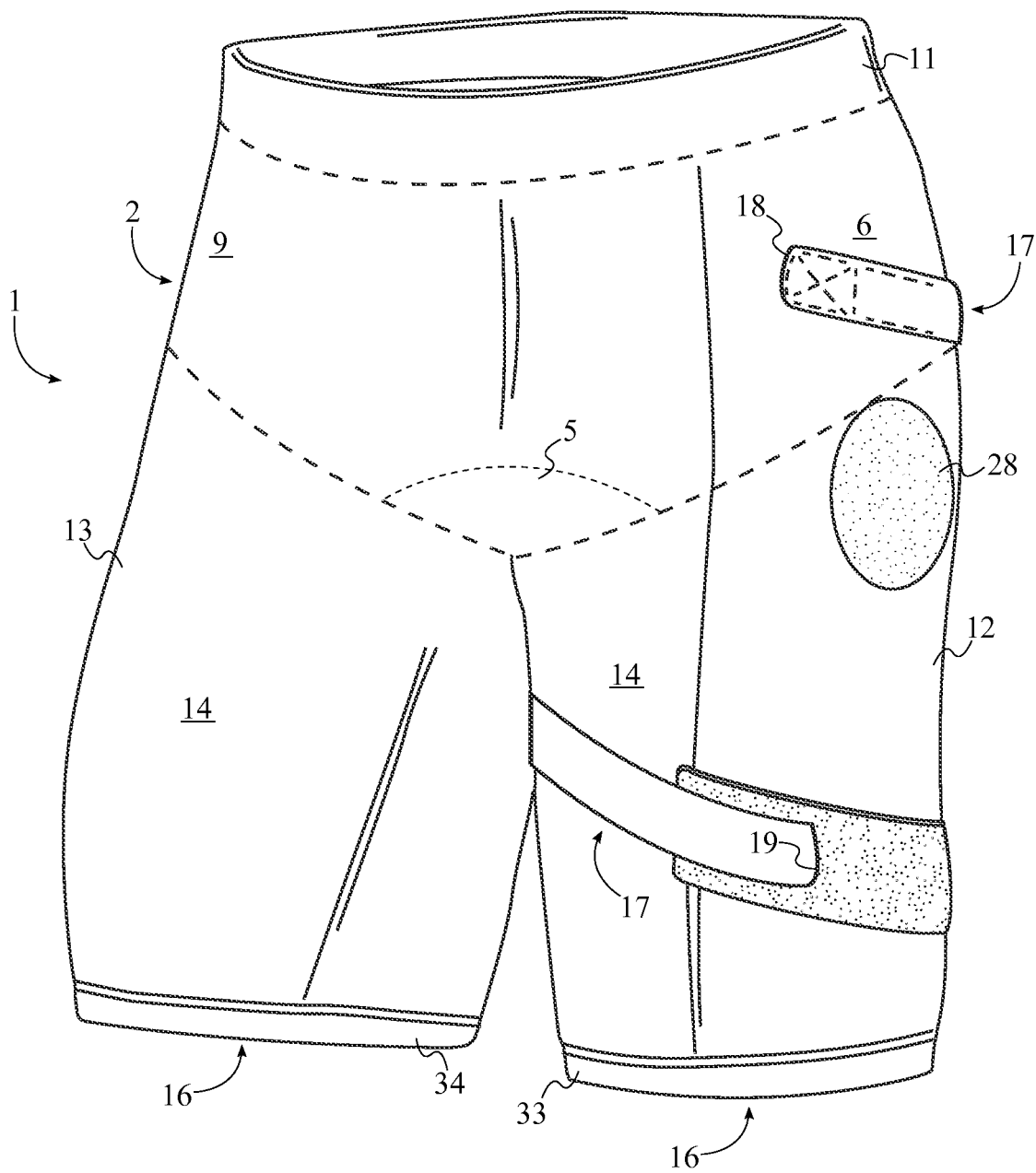
FIG. 9 is a front perspective view of the left leg lumbar hyperlordosis variant of the present invention.
Figure 10:
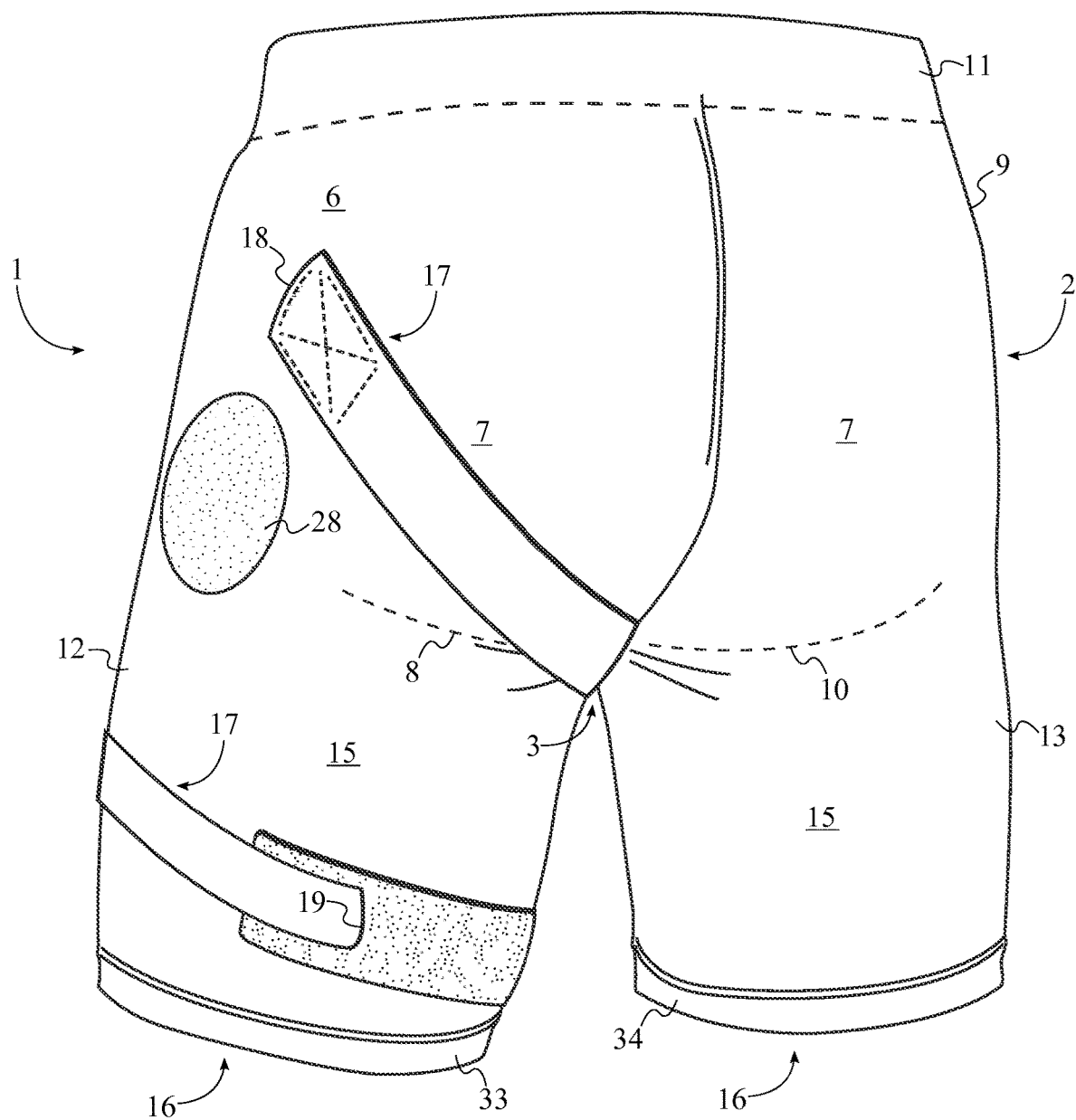
FIG. 10 is a rear perspective view of the left leg lumbar hyperlordosis variant of the present invention.

The therapeutic orientation path 22 may be situated solely on the user's leg and not around the user's waist as well. This is particularly suitable for targeting a single problematic hip or leg. In the left leg lumbar hyperlordosis embodiment of the present invention shown in FIG. 9 and FIG. 10, the beginning 23 of the therapeutic orientation path 22 is located on a left hip region 6 of the pelvic cover 2, adjacent to the waistband 11 and adjacent to a gluteal region 7 of the pelvic cover 2. This prevents the stabilizing strap 17 from exerting a force on the user's waist and additionally allows the stabilizing strap 17 to wrap downward around the user's left leg. The therapeutic orientation path 22 traverses from the beginning 23 of the therapeutic orientation path 22, about a left hip region 6 of the pelvic cover 2, adjacent to a left gluteal sulcus region 8 of the pelvic cover 2, adjacent to a crotch region 3 of the pelvic cover 2, about an anterior region 14 of the left leg short sleeve 12, and to the end 24 of the therapeutic orientation path 22. When the stabilizing strap 17 traverses about the left hip region 6 and adjacent to the left gluteal sulcus region 8, the stabilizing strap 17 is able to induce inward rotation in the user's left leg. The user's right leg and waist are unaffected. The stabilizing strap 17 then traverses adjacent to the crotch region 3 and about the anterior region 14 of the left leg short sleeve 12 in order to further rotate the user's left leg. The end 24 of the therapeutic orientation path 22 is located on the left leg short sleeve 12, opposite to the left hip region 6. This ensures that the stabilizing strap 17 is able to exert an inward rotational force along the length of the user's left leg.

Figure 11:
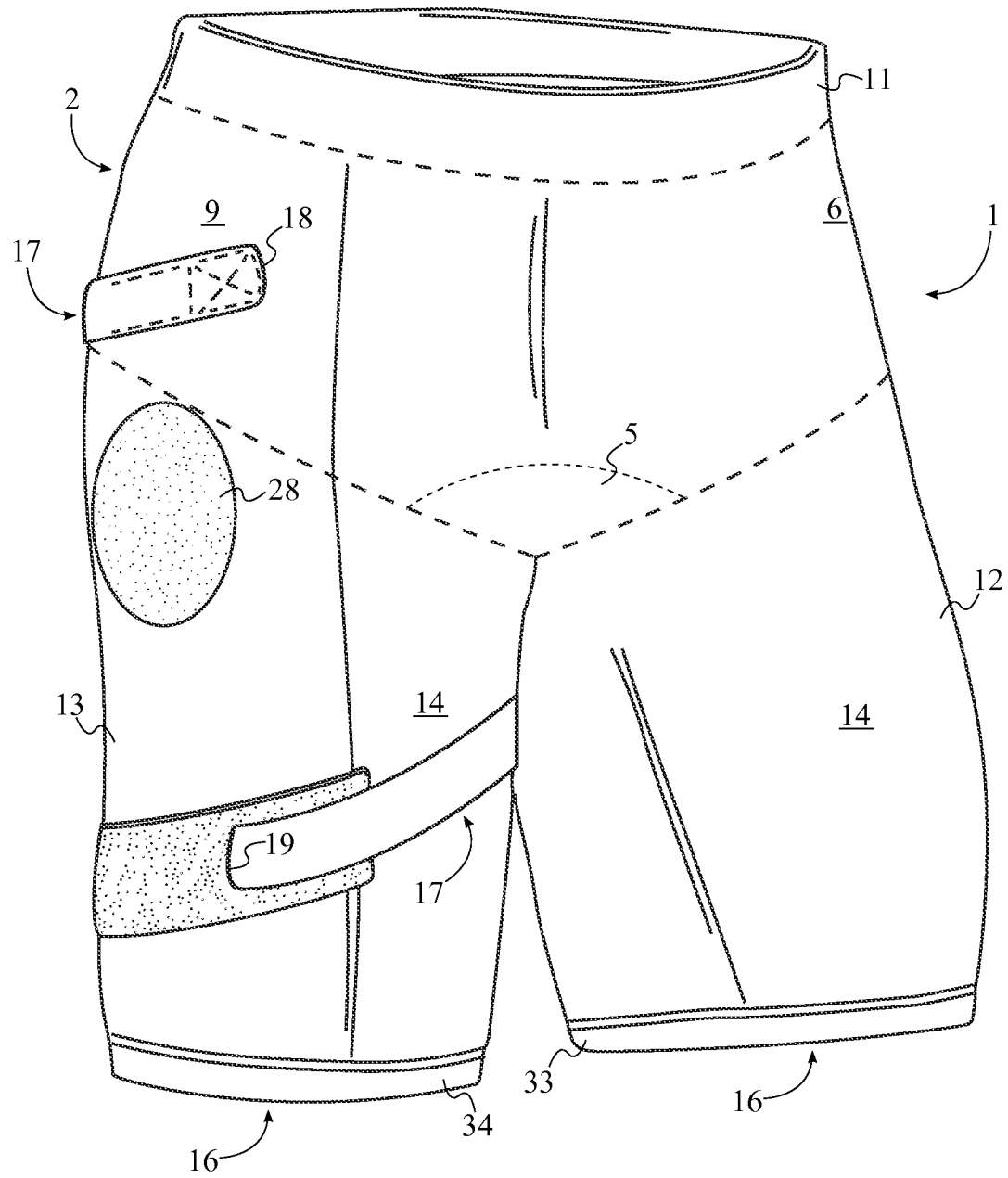
FIG. 11 is a front perspective view of the right leg lumbar hyperlordosis variant of the present invention.
Figure 12:
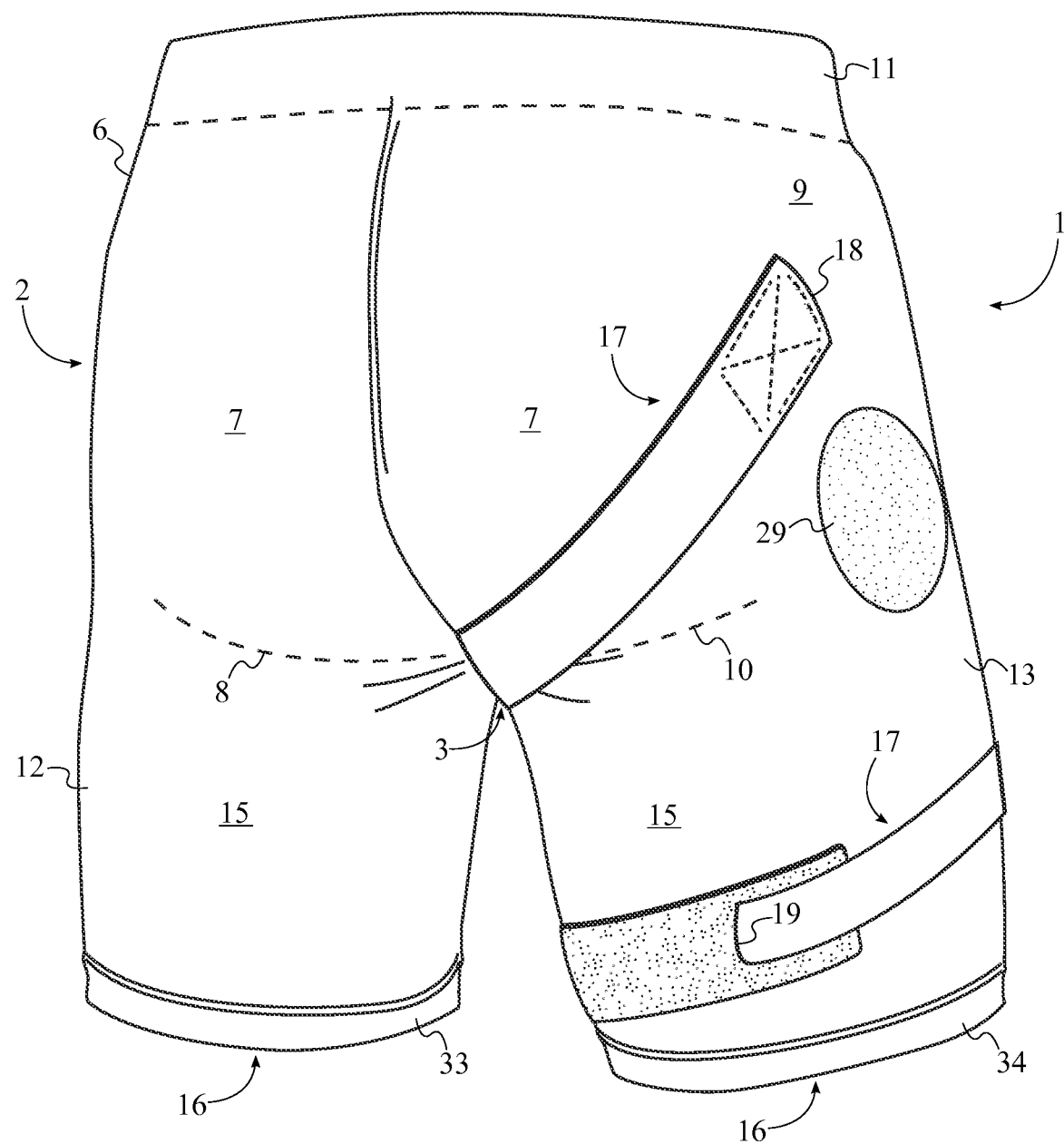
FIG. 12 is a rear perspective view of the right leg lumbar hyperlordosis variant of the present invention.

In the right leg lumbar hyperlordosis embodiment of the present invention shown in FIG. 11 and FIG. 12, the beginning 23 of the therapeutic orientation path 22 is located on a right hip region 9 of the pelvic cover 2, adjacent to the waistband 11 and adjacent to a gluteal region 7 of the pelvic cover 2. The stabilizing strap 17 thus does not exert a force on the user's waist and is able to wrap downward around the user's right leg. The therapeutic orientation path 22 traverses from the beginning 23 of the therapeutic orientation path 22, about a right hip region 9 of the pelvic cover 2, adjacent to a right gluteal sulcus region 10 of the pelvic cover 2, adjacent to the crotch region 3, about an anterior region 14 of the right leg short sleeve 13, and to the end 24 of the therapeutic orientation path 22. The stabilizing strap 17 is able to induce inward rotation in the user's right leg when the stabilizing strap 17 traverses about the right hip region 9 and adjacent to the right gluteal sulcus region 10. The user's left leg and waist remain unaffected. The stabilizing strap 17 then traverses adjacent to the crotch region 3 and about the anterior region 14 of the right leg short sleeve 13 in order to further rotate the user's right leg. The end 24 of the therapeutic orientation path 22 is located on the right leg short sleeve 13, opposite to the right hip region 9. As such, the stabilizing strap 17 is able to exert an inward rotational force along the length of the user's right leg.

Figure 13:
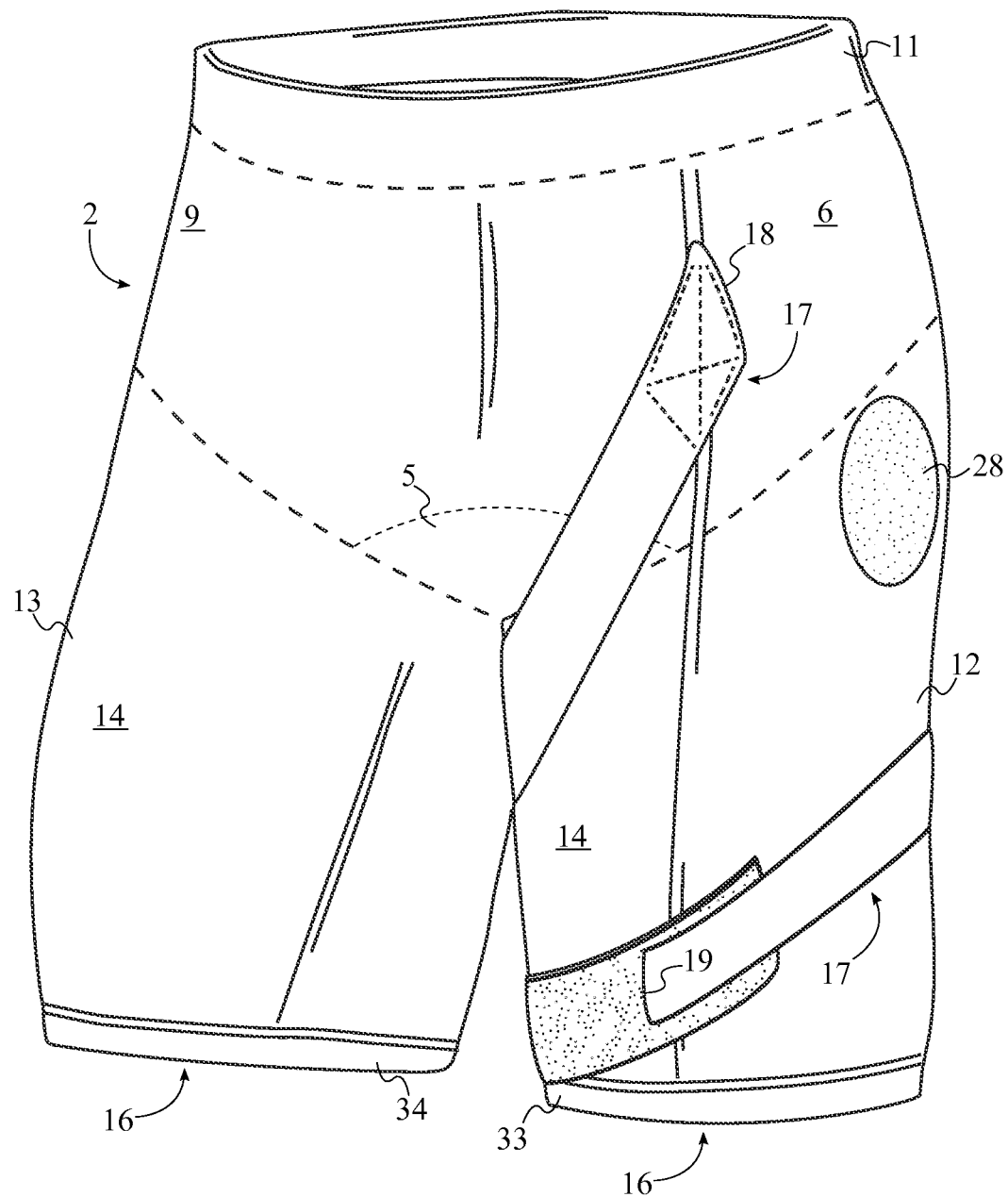
FIG. 13 is a front perspective view of the left leg lumbar hypolordosis variant of the present invention.
Figure 14:
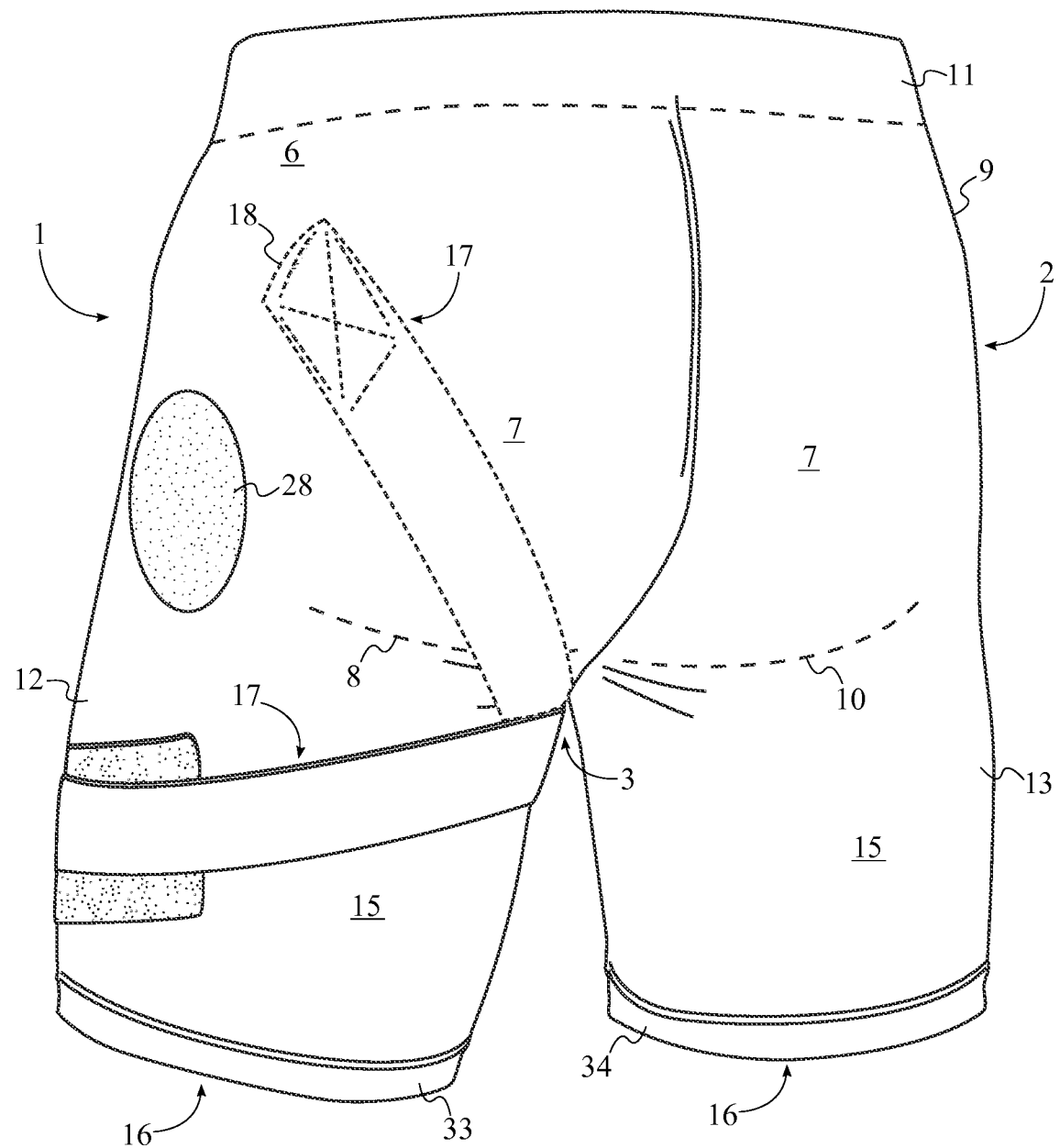
FIG. 14 is a rear perspective view of the left leg lumbar hypolordosis variant of the present invention.

In the left leg lumbar hypolordosis embodiment of the present invention shown in FIG. 13 and FIG. 14, the beginning 23 of the therapeutic orientation path 22 is located on the left hip region 6, adjacent to the waistband 11 and adjacent to the groin region 5. This prevents the stabilizing strap 17 from exerting a force on the user's waist and additionally allows the stabilizing strap 17 to wrap downward around the user's left leg. The therapeutic orientation path 22 traverses from the beginning 23 of the therapeutic orientation path 22, across the groin region 5, adjacent to the crotch region 3, adjacent to the left gluteal sulcus region 8, about the posterior region 15 to the anterior region 14 of the left leg short sleeve 12, and to the end 24 of the therapeutic orientation path 22. The stabilizing strap 17 induces outward rotation in the user's left leg when the stabilizing strap 17 traverses across the groin region 5 without affecting the user's right leg and waist. The stabilizing strap 17 then traverses adjacent to the crotch region 3, adjacent to the left gluteal sulcus region 8, and about the posterior region 15 to the anterior region 14 of the left leg short sleeve 12. This provides further rotation for the user's left leg. The end 24 of the therapeutic orientation path 22 is located on the left leg short sleeve 12, opposite to the crotch region 3. The stabilizing strap 17 is thus able to exert an outward rotational force along the length of the user's left leg.

Figure 15:
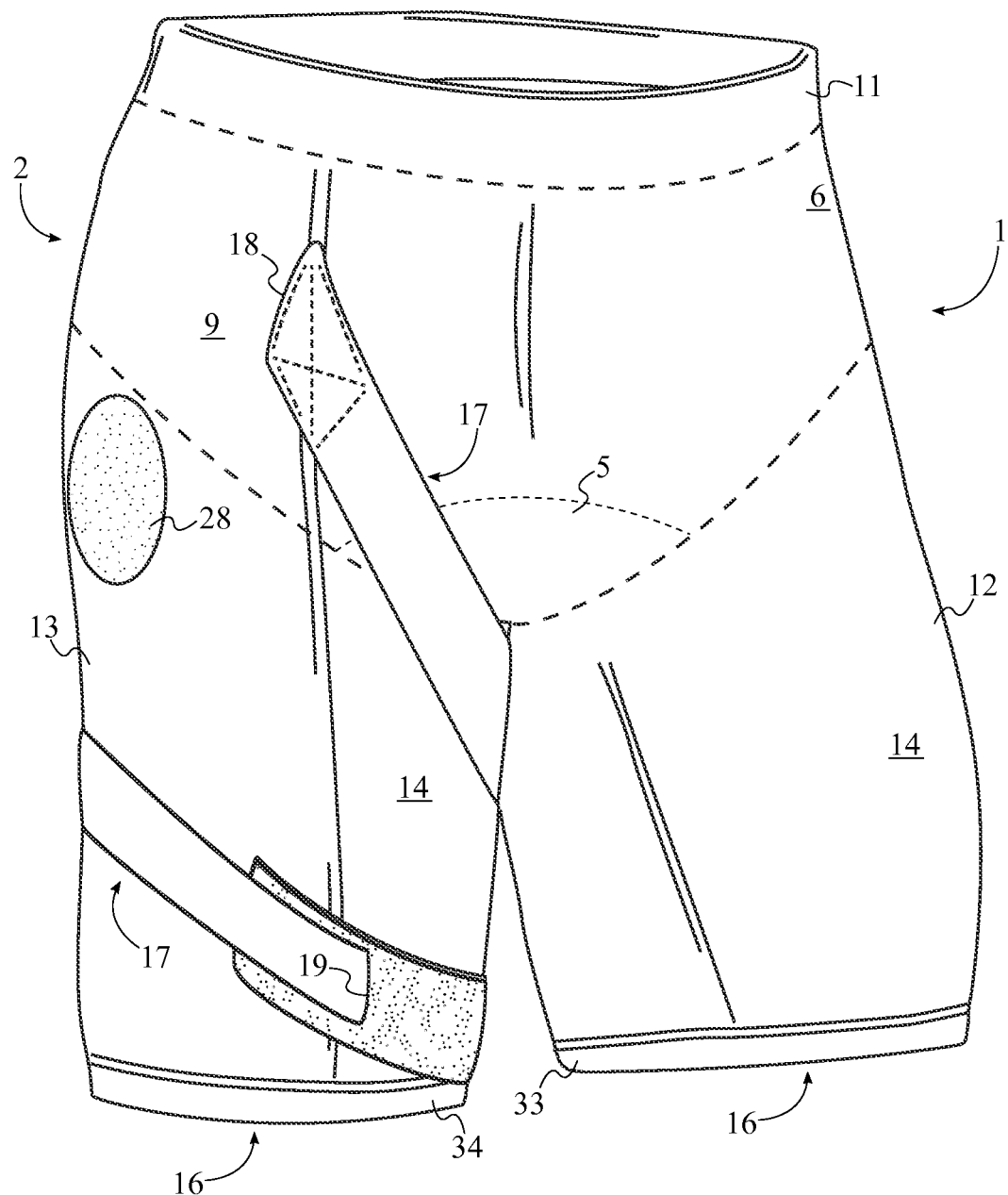
FIG. 15 is a front perspective view of the right leg lumbar hypolordosis variant of the present invention.
Figure 16:
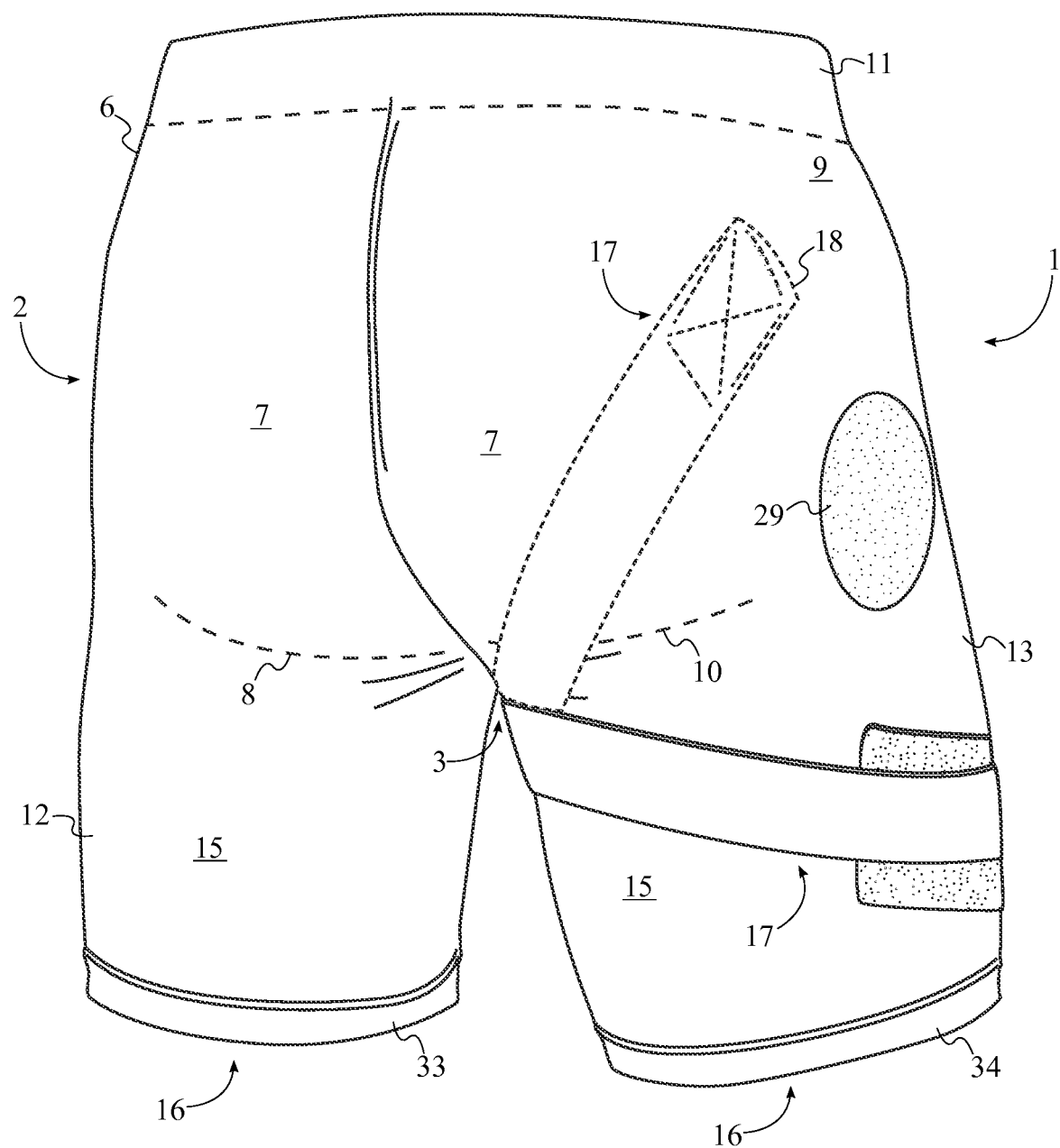
FIG. 16 is a rear perspective view of the right leg lumbar hypolordosis variant of the present invention.

The right leg lumbar hypolordosis embodiment of the present invention shown in FIG. 15 and FIG. 16 includes a beginning 23 of the therapeutic orientation path 22 that is located on the right hip region 9, adjacent to the waistband 11 and adjacent to the groin region 5. The stabilizing strap 17 thus does not exert a force on the user's waist and is able to wrap downward around the user's right leg. The therapeutic orientation path 22 traverses from the beginning 23 of the therapeutic orientation path 22, across the groin region 5, about the posterior region 15 to the anterior region 14 of the right leg short sleeve 13, adjacent to the crotch region 3, adjacent to the right gluteal sulcus region 10, and to the end 24 of the therapeutic orientation path 22. When the stabilizing strap 17 traverses across the groin region 5 and about the posterior region 15 to the anterior region 14 of the right leg short sleeve 13, outward rotation is induced in the user's right leg while the user's left leg and waist are unaffected. The stabilizing strap 17 is then able to traverse adjacent to the crotch region 3 and adjacent to the right gluteal sulcus region 10 in order to further rotate the user's right leg. The end 24 of the therapeutic orientation path 22 is located on the right leg short sleeve 13, opposite to the crotch region 3. This ensures that the outward rotational force is exerted along the length of the user's right leg.

Again with reference to FIGS. 1-16, the present invention further comprises a left femur pressure relief region 28. The left femur pressure relief region 28 is a portion of the compressive lower body garment 1 of less compressive material and ensures that the head of the user's left femur is not overly pressed into the left acetabulum of the user's pelvic bone. The left femur pressure relief region 28 is laterally positioned on the left leg short sleeve 12, opposite to the crotch region 3 about the left leg short sleeve 12. This ensures that the left femur pressure relief region 28 is positioned directly adjacent to the greater trochanter of the user's left femur. The present invention further comprises a right femur pressure relief region 29. Similar to the left femur pressure relief region 28, the right femur pressure relief region 29 is a portion of the compressive lower body garment 1 of less compressive material. The right femur pressure relief region 29 ensures that the head of the user's right femur is not overly pressed into the right acetabulum of the user's pelvic bone. The right femur pressure relief region 29 is laterally positioned on the right leg short sleeve 13, opposite to the crotch region 3 about the right leg short sleeve 13. The right femur pressure relief region 29 is thus positioned directly adjacent to the greater trochanter of the user's right femur.

With further reference to FIGS. 1-16, the present invention further comprises a left gripper ring 33 and a right gripper ring 34. The left gripper ring 33 and the right gripper ring 34 are utilized to prevent the compressive lower body garment 1 from shifting along the user's left leg and the user's right leg, respectively. The left gripper ring 33 is connected around a leg opening 16 of the left leg short sleeve 12 while the right gripper ring 34 is connected around a leg opening 16 of the right leg short sleeve 13. This ensures that the left leg short sleeve 12 and the right leg short sleeve 13 are both secured in place on the user's body while allowing the compressive lower body garment 1 to adapt to the user's natural body movement.

Figure 17:
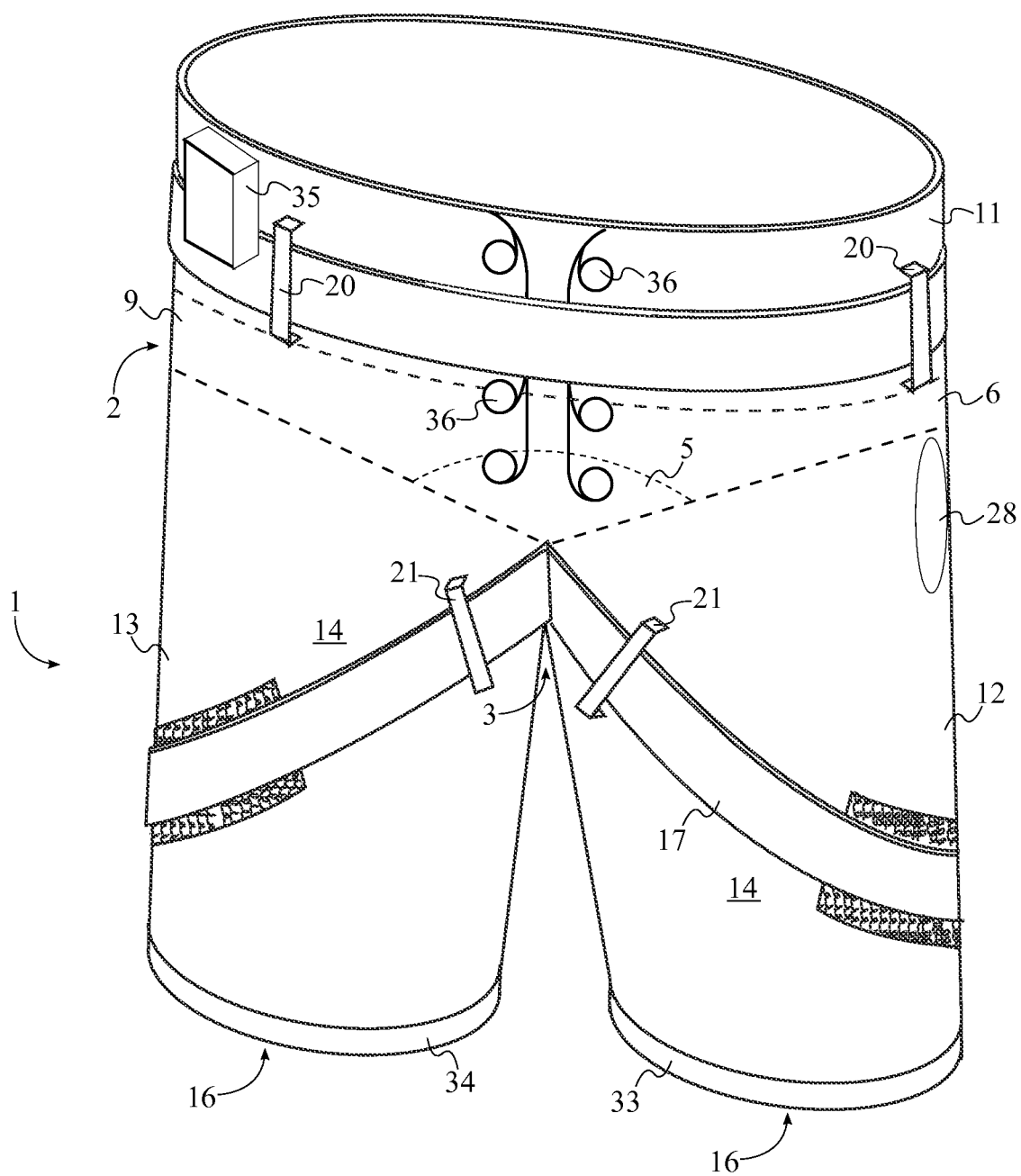
FIG. 17 is a front perspective view of the electrotherapy variant of the present invention.

The embodiment of the present invention shown in FIG. 17 further comprises an electrical muscle stimulation (EMS) impulse generation device 35 and a plurality of electrodes 36. The EMS impulse generation device 35 is utilized to generate electrical impulses that are transferred to the user's muscles when the present invention is in use. The electrical impulses are transferred to the user's muscles via the plurality of electrodes 36. As such, the plurality of electrodes 36 is electrically connected to the EMS impulse generation device 35, thus allowing the electrical impulses to flow from the EMS impulse generation device 35 to the plurality of electrodes 36. The EMS impulse generation device 35 is removably mounted to the waistband 11, allowing the user to remove the EMS impulse generation device 35 from the compressive lower body garment 1 if he or she does not wish to use the EMS impulse generation device 35. The plurality of electrodes 36 is embedded within the compressive lower body garment 1, adjacent to the pelvic cover 2. This allows the EMS impulse generation device 35 and the plurality of electrodes 36 to engage the user's muscles while supporting the user's upper body in maintaining proper posture.

Figure 19:
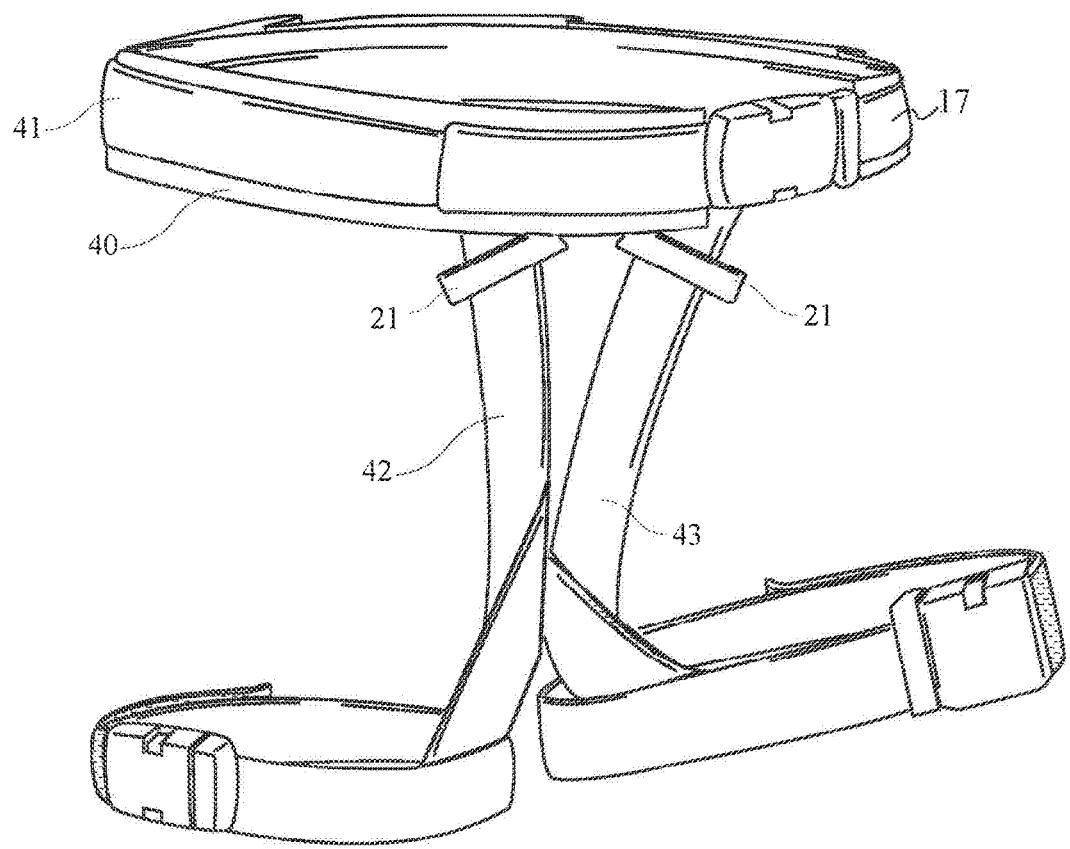
FIG. 19 is a front perspective view of the standalone stabilizing strap.

In an alternative embodiment of the present invention shown in FIG. 19, the stabilizing strap 17 is utilized without the compressive lower body garment 1. The stabilizing strap 17 further comprises a foundation strap layer 40 that is composed of rubberized gripping material to facilitate grip on the user's body when the stabilizing strap 17 is worn. An external strap layer 41 is superimposed onto and secured to the foundation strap layer 40. The external strap layer 41 and the foundation strap layer 40 may be secured to each other via hook and loop fasteners or a similar mechanism. The external strap layer 41 and the foundation strap layer 40 are able to tilt the user's pelvis. A left leg connection strap 42 and a right leg connection strap 43 that provide rotational motion to the user's thighs are attached to the external strap layer 41 and the foundation strap layer 40. The left leg connection strap 42 and the right leg connection strap 43 are attachable to the external strap layer 41 and the foundation strap layer 40 via buckles, hook and loop fasteners, or a similar mechanism. This alternative embodiment of the present invention allows the stabilizing strap 17 to be worn over the user's normal clothing to achieve a therapeutic effect.

Although the present invention has been explained in relation to its preferred embodiment, it is understood that many other possible modifications and variations can be made without departing from the scope of the present invention as hereinafter claimed.

What is claimed is:

1. A dynamic lumbar realignment system comprising:
   a stabilizing strap;
   a therapeutic orientation path;
   a plurality of strap-supporting attachment loops;
   a plurality of strap-guiding attachment loops, wherein each of the plurality of strap-guiding attachment loops are configured to receive the stabilizing strap through the respective strap-guiding attachment loop, and wherein the therapeutic orientation path is at least partially defined by the plurality of strap-guiding attachment loops;
   the stabilizing strap being positioned onto a body garment with a pelvic cover, a waistband, a left thigh short sleeve and a right thigh short sleeve along the therapeutic orientation path through the plurality of strap-guiding attachment loops and the plurality of strap-supporting attachment loops, wherein each of the plurality of strap-guiding attachment loops are attached to and positioned on the body garment such that, when each of the plurality of strap-guiding attachment loops receive the stabilizing strap, the stabilizing strap is guided along the therapeutic orientation path by the plurality of strap-guiding attachment loops;
   the stabilizing strap extending from an anterior region of the left thigh short sleeve upwardly to a crotch region of the pelvic cover and further around an inner portion of the left thigh short sleeve from the crotch region of the pelvic cover, and from an anterior region of the right thigh short sleeve upwardly to the crotch region of the pelvic cover and further around an inner portion of the right thigh short sleeve from the crotch region of the pelvic cover;
   the stabilizing strap comprising a first strap end and a second strap end;
   the plurality of strap-supporting attachment loops being externally positioned about the waistband;
   the plurality of strap-guiding attachment loops being externally positioned on the pelvic cover, the left thigh short sleeve and the right thigh short sleeve;
   the therapeutic orientation path comprising a beginning and an end;
   the first strap end being attached at the beginning;
   the second strap end being attached at the end, wherein a first strap-guiding attachment loop of the plurality of strap-guiding attachment loops is positioned along the therapeutic orientation path adjacent to a front crotch region of the left thigh short sleeve and directs the strap from the front crotch region of the left thigh short sleeve upwards between the left thigh short sleeve and the right thigh short sleeve towards a rear crotch region of the left thigh short sleeve, wherein a second strap-guiding attachment loop of the plurality of strap-guiding attachment loops is positioned along the therapeutic orientation path adjacent to a front crotch region of the right thigh short sleeve and directs the strap from the front crotch region of the right thigh short sleeve upwards between the left thigh short sleeve and the right thigh short sleeve towards a rear crotch region of the right thigh short sleeve, and wherein the stabilizing strap is arranged along the therapeutic orientation path spanning from the beginning, along an outside of the left thigh short sleeve to the first strap-guiding attachment loop, between the left thigh short sleeve and the right thigh short sleeve to the plurality of strap-supporting attachment loops about the waistband, between the left thigh short sleeve and the right thigh short sleeve, to the second strap-guiding attachment loop, and along an outside of the right thigh short sleeve to the end; and
   the stabilizing strap being arranged through the plurality of strap-guiding attachment loops along the therapeutic orientation path in such a way that abdominal compression, pelvic tilt and thigh rotation are configured to be dynamically integrated so as to provide and generate a therapeutic effect, the stabilizing strap being configured to tilt the pelvis of a user backward and rotate both the left thigh and the right thigh of the user inwardly when the stabilizing strap is received by the plurality of strap-guiding attachment loops along the therapeutic path.

2. The dynamic lumbar realignment system as claimed in claim 1 comprising:
   the therapeutic orientation path, as at least partially defined by the plurality of strap-guiding attachment loops, comprising a first portion, a second portion and a third portion;
   the first portion being connected in between the beginning and the second portion;
   the second portion being connected in between the first portion and the third portion;
   the third portion being connected in between the second portion and the end;
   the beginning being located at a posterior region of the left thigh short sleeve opposite to the pelvic cover;

the first portion traversing about the left thigh short sleeve from the posterior region of the left thigh short sleeve to the anterior region of the left thigh short sleeve, to the crotch region of the pelvic cover and adjacent to a buttock crevice region of the pelvic cover;

the second portion traversing about the waistband;

the third portion traversing about the right thigh short sleeve from a posterior region of the right thigh short sleeve to the anterior region of the right thigh short sleeve, to the crotch region of the pelvic cover and adjacent to the buttock crevice region of the pelvic cover; and the end being located at the posterior region of the right thigh short sleeve opposite to the pelvic cover.

3. The dynamic lumbar realignment system as claimed in claim 2 comprising:

the first portion and the third portion traversing adjacent to each other on the buttock crevice region of the pelvic cover.

4. The dynamic lumbar realignment system as claimed in claim 1 further comprising:

a left femur pressure relief region configured to be positioned over a greater trochanter of a left femur of the user and a right femur pressure relief region configured to be positioned over a greater trochanter of a right femur of the user.

5. The dynamic lumbar realignment system as claimed in claim 1, wherein the stabilizing strap comprises an elastic material.

6. The dynamic lumbar realignment system as claimed in claim 1 comprising:

the stabilizing strap comprising a first elastic section, a second elastic section and a non-elastic section; and the non-elastic section being connected in between the first elastic section and the second elastic section.

7. The dynamic lumbar realignment system as claimed in claim 1 comprising:

the body garment further comprising a left gripper ring and a right gripper ring, the left gripper ring being connected around a thigh opening of the left thigh short sleeve, the right gripper ring being connected around a thigh opening of the right thigh short sleeve.

* * * * *